United States Patent

Gough et al.

Patent Number: 5,585,530
Date of Patent: Dec. 17, 1996

[54] TRANSHYDROGENATION

[75] Inventors: Arthur Gough, Northallerton; Stephen K. Turner, Guisborough, both of England

[73] Assignee: Institut Francais Du Petrole, Rueil-Malmaison Cedex, France

[21] Appl. No.: 140,094

[22] PCT Filed: Apr. 16, 1992

[86] PCT No.: PCT/GB92/00699

§ 371 Date: Jun. 8, 1994

§ 102(e) Date: Jun. 8, 1994

[87] PCT Pub. No.: WO92/19575

PCT Pub. Date: Nov. 12, 1992

[30] Foreign Application Priority Data

May 3, 1991 [GB] United Kingdom ............ 9109691
Oct. 14, 1991 [GB] United Kingdom ............ 9121732

[51] Int. Cl.$^6$ ............ C07C 5/02; C07C 5/52; C07C 5/09; C07C 5/327

[52] U.S. Cl. ............ 585/257; 585/616; 585/627; 585/629; 585/630; 585/631; 585/656; 585/660; 585/661; 585/662; 585/663

[58] Field of Search ............ 585/257, 616, 585/627, 629, 630, 631, 656, 660, 661, 662, 663

[56] References Cited

U.S. PATENT DOCUMENTS

| | | | |
|---|---|---|---|
| 3,950,447 | 4/1976 | Gryaznov | 585/252 |
| 4,546,204 | 10/1985 | Parris | 585/314 |
| 4,684,455 | 8/1987 | Parris et al. | 585/257 |
| 4,975,097 | 12/1990 | Harandi et al. | 44/77 |
| 5,176,719 | 1/1993 | Harandi et al. | 44/449 |
| 5,227,552 | 7/1993 | Chang et al. | 585/257 |

Primary Examiner—Asok Pal
Assistant Examiner—E. D. Irzinski
Attorney, Agent, or Firm—Cushman Darby & Cushman, L.L.P.

[57] ABSTRACT

A process for the production of olefins comprises dehydrogenating at least one hydrogen-donor hydrocarbon that is essentially free from olefinic unsaturation, e.g. a paraffin, in the presence of a dehydrogenation catalyst and in the presence of at least one hydrogen-acceptor hydrocarbon that is more highly unsaturated than a mono-olefin, e.g. a diene and/or acetylene, under conditions effective to cause at least part of said hydrogen-donor hydrocarbon to be dehydrogenated and at least part of the hydrogen-acceptor to be hydrogenated. The amount of hydrogen-acceptor is such that there are 0.5 to 20 moles of said hydrogen-donor for each mole of hydrogen-acceptor. Preferably the amount of said hydrogen-acceptor hydrocarbon hydrogenated is such that the heat of hydrogenation of said hydrogen-acceptor hydrocarbon provides at least 25% of the heat required for dehydrogenation of said hydrogen-donor hydrocarbon. In a preferred form of the invention, a hydrocarbon stream containing a hydrogen-acceptor is a $C_4$ stream from a dydrocarbon cracker and is reacted with a paraffin such as propane or 2-methylpropane as the hydrogen-donor; after separation of propene and/or 2-methylpropene, at least part of the product is recycled to the cracker.

9 Claims, No Drawings

TRANSHYDROGENATION

This application is a 371 of PCT/GB92/00699 filed Apr. 16, 1992.

This invention relates to transhydrogenation as a method of effecting dehydrogenation of a hydrocarbon that is free from olefinic unsaturation, for example a paraffin, to produce olefins.

BACKGROUND TO THE INVENTION

The dehydrogenation of hydrocarbons, such as paraffins, to produce olefins is an endothermic reaction and requires the input of a considerable amount of heat. For thermodynamic reasons, it has to be effected at relatively high temperatures. However at high temperatures there is also the possibility of thermal cracking. As a result the temperatures that can be employed in practice are relatively limited and so high conversions to the desired olefins are not thermodynamically possible.

In the present invention a transhydrogenation process is employed to effect dehydrogenation of hydrocarbons to olefins. In a transhydrogenation process a hydrogen-donor, such as a paraffin, is catalytically dehydrogenated in the presence of a hydrogen-acceptor such as an unsaturated compound so that the latter is hydrogenated at the same time. In effect, although this may not be the actual reaction mechanism, hydrogen is transferred from the hydrogen-donor, producing an olefin, to the hydrogen-acceptor, hydrogenating the latter.

Transhydrogenation processes for the production of olefins have been described for example in U.S. Pat. No. 3,267,170 and U.S. Pat. No. 4,684,755 wherein a hydrogen-donor such as propane, n-butane, or 2-methylpropane, has been reacted over a catalyst with a mono-olefin such as ethene as a hydrogen-acceptor. In the reaction, the hydrogen-donor is dehydrogenated to the corresponding olefin while the hydrogen-acceptor is hydrogenated to the corresponding paraffin eg ethane. It is seen that there is no net production of olefin since for each mole of olefin produced from the paraffin, one olefin molecule is consumed as the hydrogen-acceptor. Indeed there may be a net reduction in the olefin content since the aforesaid U.S. Pat. No. 3,267,170 discloses that the hydrogen-donor may be dehydrogenated further, to the corresponding diene, and/or that a mixture of the paraffin and the corresponding olefin may be dehydrogenated, by reaction with the hydrogen-acceptor olefin, to give a mixture of the olefin and diene corresponding to the paraffin. For example, it is suggested that a mixture of butane and butene-1 or butene-2, may be reacted with ethene as the hydrogen-acceptor olefin to give a mixture of butene-1, butene-2, and butadiene-1,3.

We have now discovered that that type of process may be used to give a net production of olefins by using a more highly unsaturated compound, such as a diene or acetylene, as the hydrogen-acceptor in place of the mono-olefin hydrogen-acceptors heretofore employed.

The use of more unsaturated hydrocarbons than mono-olefins as hydrogen acceptors has been described in GB-A-1046780 where it was proposed to produce cycloalkenes by the selective hydrogenation of a more highly unsaturated cycloalkene, such as cyclododeca-1:5:9-triene or cycloocta-1:5-diene, by contacting that cycloalkene with a compound having an ethylenically unsaturated hydrocarbon ring containing six carbon atoms, eg cyclohexene, as the hydrogen-donor.

As will be described hereinafter, in the present invention the hydrogen-acceptor preferably contains 3 to 5 carbon atoms, and is particularly propyne, propadiene, butadiene-1,3,2-methylbutadiene-1,3, cyclopentadiene, and/or pentadiene-1,3.

A process wherein a feedstock stream containing 2-methylpropane and n-butane, mixed with a recycle stream containing a small amount of butadiene, is reacted over a dehydrogenation catalyst to produce a mixture of butanes, butenes and butadiene is described in EP-A-166359: a butadiene-containing stream separated from the product stream is used as the aforesaid recycle stream. In this process, the amount of butadiene added to the fresh feedstock via the recycle stream is relatively small so that the amount of butadiene hydrogenation occurring is small in relation to the amount of dehydrogenation of the butanes taking place.

BRIEF DESCRIPTION OF THE INVENTION

The present invention provides a process for the production of olefins comprising dehydrogenating at least one hydrogen-donor hydrocarbon that is essentially free from olefinic unsaturation, eg a paraffin, in the presence of a dehydrogenation catalyst and in the presence of at least one hydrogen-acceptor hydrocarbon that is more highly unsaturated than a mono-olefin, eg a diene and/or acetylene, under conditions effective to cause at least part of said hydrogen-donor hydrocarbon to be dehydrogenated and at least part of the hydrogen-acceptor to be hydrogenated. The amount of hydrogen-acceptor is such that there are 0.5 to 20 moles of said hydrogen-donor for each mole of hydrogen-acceptor. Preferably the amount of said hydrogen-acceptor hydrocarbon hydrogenated is such that the heat of hydrogenation of said hydrogen-acceptor hydrocarbon provides at least 25% of the heat required for dehydrogenation of said hydrogen-donor hydrocarbon.

GENERAL DESCRIPTION OF THE INVENTION

In the absence of a hydrogen-acceptor compound, dehydrogenation reactions generally are endothermic and, to obtain a useful conversion, have to be effected at high temperatures. At such temperatures dehydrogenation is usually accompanied by thermal cracking of the hydrogen-donor with the formation of carbon deposits. Such carbon deposits tend to build up on the catalyst de-activating the latter: frequent regeneration of the catalyst is required wherein the deposited carbon is burnt off by subjecting the catalyst to a stream of a heated oxygen-containing gas such as air. We have found that the transhydrogenation of the present invention may be effected under reaction conditions, eg lower temperatures or in the presence of hydrogen, at which only little dehydrogenation of the hydrogen-donor would take place in the absence of the hydrogen-acceptor and, under such conditions, there may be less tendency to carbon deposition even though, in the absence of the hydrogen-donor, such hydrogen-acceptor compounds may exhibit a significant tendency to thermal cracking with carbon deposition.

By effecting the dehydrogenation of the hydrogen-donor in the presence of the hydrogen-acceptor, at least some of the heat required for the dehydrogenation is in effect provided by hydrogenation of the hydrogen-acceptor. In the present invention, preferably at least 25%, particularly at least 50%, and more particularly at least 70%, of the heat required for dehydrogenation of the hydrogen-donor is in effect provided by the exothermic hydrogenation of the hydrogen-acceptor. As a result, the reaction conditions may be adjusted such that the reaction is net endothermic, net exothermic or thermally neutral: also the reaction can be effected in the presence of hydrogen and the reaction conditions may be such that there is a net production or net consumption of hydrogen. The ability to operate in the presence of hydrogen may be advantageous to decrease the tendency to coke formation.

Although a gross over simplification, for the purposes of the present invention, the heat required for dehydrogenation of the hydrogen-donor is deemed to be the heat required to effect the removal of one molecule of hydrogen from each molecule of hydrogen-donor dehydrogenated. It is assumed for the purposes of calculation that there is no re-arrangement or further reaction of the dehydrogenated hydrocarbon, and that it is a terminal portion of the molecule, eg a >CH—CH$_3$ group, that is dehydrogenated: thus it is assumed that propane is dehydrogenated to propene; n-butane to butene-1; 2-methylpropane to 2-methyl-propene etc. The amount of hydrogen-donor that is dehydrogenated is computed as the amount present in the feed, less the amount, if any, in the product. The heat of dehydrogenation is the number of moles of hydrogen-donor dehydrogenated multiplied by the heat of dehydrogenation of a mole of hydrogen-donor. The heat of dehydrogenation of a mole of hydrogen-donor is computed by subtracting the enthalpy of a mole of the hydrogen-donor from the sum of the enthalpies of a mole of hydrogen and a mole of the assumed dehydrogenation product, the enthalpies being those of the various components at the reaction temperature. The heat of hydrogenation of the hydrogen-acceptor is similarly calculated on the assumption that each molecule of hydrogen-acceptor is hydrogenated by the addition of one molecule of hydrogen, again with no re-arrangement or further hydrogenation. Thus propyne and propadiene are assumed to be hydrogenated to propene; butadiene to butene-1; 2-methylbutadiene-1,3 to 2-methylbutene-1 etc. The amount of hydrogen-acceptor hydrogenated is deemed to be the amount thereof in the feed, less the amount, if any, in the product. The heat of hydrogenation is the number of moles of hydrogen-acceptor hydrogenated multiplied by the heat of hydrogenation of a mole of hydrogen-acceptor. The heat of hydrogenation of a mole of hydrogen-acceptor is computed by subtracting the sum of the enthalpies of a mole of hydrogen and a mole of hydrogen-acceptor from the enthalpy of a mole of the assumed hydrogenation product, the enthalpies being those of the various components at the reaction temperature. For the purposes of the calculation, it is assumed that where the reaction is effected under non-isothermal, eg adiabatic, conditions, the reaction temperature is the exit temperature.

As a simple hypothetical illustration if 90 moles of propane are dehydrogenated at 550° C. in the presence of 10 moles of butadiene giving a product containing, inter alia, 70 moles of propane and 0.5 moles of butadiene, it is seen that 20 moles of propane have been dehydrogenated and 9.5 moles of butadiene have been hydrogenated. Assuming that the enthalpies (kJ/mole) at 550° C. are as follows:

| hydrogen | 16.1 | propane | 65.2 | propene | 54.5 |
| butadiene | 67.5 | butene-1 | 76.0 | | | the heat of dehydrogenation of the propane is

20 * (54.5+16.1−65.2)=108.0 kJ while the heat of hydrogenation of the butadiene is 9.5 * (76.0−67.5−16.1)=−72.2 kJ Hence the heat of hydrogenation of the butadiene represents 72.2/108.0, ie 67%, of the heat required for the dehydrogenation of the propane.

It will be appreciated that in practice in this example, the product will contain, in addition to the aforesaid products propene and butene-1, and unreacted butadiene and propane, other butenes (which have lower enthalpies than butene-1), and butanes resulting from the hydrogenation of the butenes. These further reactions will provide a further contribution to the heat required for dehydrogenation of the propane, and indeed may be sufficient to provide all the required heat of dehydrogenation: however for the purposes of describing the present invention, such further contributions towards the heat of dehydrogenation of the hydrogen-donor are ignored when determining the proportion of the heat required for dehydrogenation of the hydrogen-donor that is provided by hydrogenation of the hydrogen-acceptor.

Where, for example as a result of isomerisation and/or further hydrogenation, the product contains a compound that is classifiable as a hydrogen-donor that is not present in the feed, or where the amount of such a compound in the product is greater than the amount thereof in the feed, then that compound is ignored when computing the heats of hydrogenation and dehydrogenation.

In the present invention dehydrogenation of the hydrogen-donor takes place: generally the conditions are such that some dehydrogenation thereof would take place even if the hydrogen-acceptor was omitted. The amount of such dehydrogenation that would occur in the absence of the hydrogen-acceptor generally increases as the reaction temperature increases. As a consequence, as the reaction temperature is increased, the proportion of the heat required for dehydrogenation that is supplied by hydrogenation of the hydrogen-acceptor will generally decrease. However the presence of substantial amounts of the hydrogen-acceptor may also have a significant effect on the equilibrium such that a favourable conversion of hydrogen-donor to olefin is obtained under conditions which could not be achieved by dehydrogenation of the hydrogen-donor alone because of thermodynamic limitations. Also, since dehydrogenation reactions result in an increase in the number of molecules, dehydrogenation reactions are favoured by operation at low pressures. However transhydrogenation produces no increase in the number of molecules, and so the need to operate at low pressures to obtain a favourable conversion is less important: consequently, where it is desired to operate the dehydrogenation process at elevated pressures, the need for large proportions of inert diluents so as to maintain the reactants partial pressures low, is decreased. There may however be a small proportion of additional molecules produced by side reactions.

The operating conditions, eg temperatures and pressures, employed will depend on the choice of catalyst, the hydrogen partial pressure, and the nature of the hydrogen-donor and hydrogen-acceptor. Preferably the conditions are such that a total of at least 10% by weight of the hydrogen-donor is dehydrogenated.

The total pressure is preferably in the range 0.3 to 20, particularly 0.5 to 10, and more particularly in the range 1 to 5, bar abs. The partial pressure of hydrogen-donor plus hydrogen-acceptor is preferably in the range 0.1 to 20, particularly 0.1 to 5, bar abs. The temperature is preferably in the range 200° to 800° C., particularly 450° to 700° C.

Although elevated temperatures are required, often necessitating preheating of the reactants, since the process is preferably operated such that at least 25% of the heat required for the dehydrogenation of the hydrogen-donor is supplied by hydrogenation of the hydrogen-acceptor, far less heat input is required than in dehydrogenation in the absence of the hydrogen-acceptor. Thus heat can be recovered from the products and by feed/effluent heat exchange used to provide most, if not all, of the heat required for the reaction.

The amount of hydrogen-donor is from 0.5 to 20, particularly 1 to 10, and more particularly 2 to 10, moles for each mole of hydrogen-acceptor employed. Preferably the molar amount, if any, of hydrogen added is less than 10 times the total molar amount of hydrocarbon present.

The reaction may be effected in the presence of a diluent such as steam which, in some cases, may suppress coke formation and/or may serve to activate the catalyst. Methane may alternatively or additionally be used as a diluent.

The hydrogen-acceptor stream may typically comprise dienes and/or acetylenes alone or in admixture with mono-olefins and/or paraffins. Examples of suitable hydrogen-acceptor streams include propyne, propadiene, butadiene-1,2, butadiene-1,3, and mixtures thereof, eg propyne plus propadiene; $C_4$ streams such as a mixed $C_4$ stream from a steam cracker; and $C_5$ gasoline, and/or full range pygas, streams from a cracker. Butadiene-1,2 is often present as a small proportion of the total butadienes, and for simplicity hereinafter, except where the contrary is indicated, when reference is made to butadiene we mean a mixture of butadienes containing butadiene-1,3 and not more than 20% by weight of butadiene-1,2.

The hydrogen-donor stream is preferably a paraffin stream containing 2 or more carbon atoms, for example ethane, propane, n-butane, 2-methylpropane, mixed $C_4$ paraffins, paraffins containing 5 or more carbon atoms, or it may be ethylbenzene or a similar alkyl aromatic with alkyl groups of 2 or more carbon atoms. It will be appreciated that the hydrogen-donor stream may contain, in addition to at least one hydrogen-donor compound that is free from olefinic unsaturation, other components such as mono-olefins.

In some cases, by suitable selection of the reaction conditions and/or catalyst, some desired isomerisation of the reactants may accompany the transhydrogenation reaction.

It may be convenient, although not essential, that the hydrogen-acceptor and hydrogen-donor compounds contain the same number of carbon atoms: in this way the olefin produced will also contain the same number of carbon atoms. As examples there may be quoted propane with propyne and/or propadiene; and 2-methyl-propane and/or n-butane with butadiene or with a mixed $C_4$ stream containing butadiene.

The process is effected in the presence of a dehydrogenation catalyst. By the term dehydrogenation catalyst we mean a catalyst that will effect dehydrogenation of the hydrogen-donor under the conditions employed. The catalyst employed will depend on the nature of the hydrogen-acceptor and hydrogen-donor compounds. Suitable catalysts include noble metals, eg platinum and/or other platinum group metals such as palladium, on a support such as alumina; such catalysts modified with other species, eg Group IV elements such as tin; chromia, alone or in conjunction with a platinum group metal or iron oxide, on a support such as alumina, zirconia and/or alkaline earth oxides, especially those stabilised for use at high temperatures; platinum group metals supported on such supports. Sulphided versions of the above catalysts and/or molybdenum sulphide may also be used. However, unless the reaction is effected in the presence of added hydrogen and/or the catalyst is sulphided or otherwise moderated, platinum on alumina may not be suitable for some processes as some polyunsaturated compounds, eg butadiene, may be so strongly adsorbed that there is negligible reaction with the hydrogen-donor, eg paraffin. Chromia, optionally in admixture with a platinum group metal, and preferably doped with alkali, on alumina is particularly suitable. Another particularly suitable catalyst is a mixture of platinum and tin, supported on alumina, again preferably doped with alkali. In alkali doped catalysts, the alkali is preferably potassium or cesium.

Where the process conditions are such that coke is deposited on the catalyst, the catalyst may be regenerated periodically by passing hot air, optionally mixed with nitrogen, over the catalyst. Other regeneration processes known in the dehydrogenation art, using eg steam and/or hydrogen, may be employed. In some cases it may be desirable to employ two or more transhydrogenation units so that while one or more units is on-line the other unit or units are undergoing regeneration. Alternatively a moving catalyst bed type of reactor may be employed.

Adjustment of the five main reaction variables, viz total pressure, temperature, residence time, hydrogen-donor/hydrogen-acceptor ratio, and hydrogen partial pressure, enables control to be exercised over the product composition and can determine whether the reaction is a net generator or consumer of hydrogen or is a net generator or consumer of heat.

Specific forms of the invention will now be described with reference to particular hydrogen-acceptors and hydrogen-donors.

Hydrogen-acceptors Containing 4 or More Carbon Atoms

In this category are included $C_4$ streams and "gasoline" streams containing polyunsaturated compounds such as butadiene, 2-methylbutadiene-1,3, cyclopentadiene, and pentadiene-1,3. Such streams generally result from hydrocarbon cracking operations: often the aim of such cracking operations is to produce olefins containing up to about 5 carbon atoms. Thus such olefins are conventionally produced by cracking a hydrocarbon feedstock such as naphtha, LPG, or gas-oil. This process gives a mixture of hydrogen and saturated, unsaturated, and aromatic hydrocarbons.

The precise composition of the cracker product will of course depend on the nature of the feedstock and the cracker operating conditions; a typical percentage composition (by weight) of the product of cracking naphtha is as follows:

| hydrogen | 1 | benzene | 6 |
|---|---|---|---|
| methane | 16 | toluene | 3 |
| ethene | 32 | $C_8$ aromatics | 2 |
| propene | 16 | fuel oil | 4 |
| $C_4$ hydrocarbons | 8 | others | 12 |

The product is usually separated, eg by distillation, into a number of streams, such as $C_3$, $C_4$, and $C_5$ streams. By means of the present invention polyunsaturated compounds in these streams can be used as hydrogen-acceptors to improve the yield of olefins. A typical approximate weight percentage composition for a $C_4$ stream is as follows:

| butadiene | 51 | 2-methylpropene | 21 |
|---|---|---|---|
| butene-1 | 12 | n-butane | 7 |
| t-butene-2 | 4 | 2-methylpropane | 2 |
| c-butene-2 | 3 | | |

The butadiene content of the cracker $C_4$ stream is sometimes recovered for sale as pure butadiene and the remainder of the stream can then be used as a source of 2-methylpropene, recycled to the cracker furnace, or subjected to other treatments. While 2-methylpropene is a valuable material, for example it may be used to manufacture methyl t-butyl ether (MTBE), there may be insufficient 2-methylpropene present to justify the separation thereof. Consequently the value of the $C_4$ products may not justify such separation and treatment steps and so the whole $C_4$ stream, including the butadiene and 2-methyl-propene, may be recycled to the cracking furnace. On cracking, this $C_4$ stream does not give very high yields of valuable gaseous olefins and typically only 75–80% of the $C_4$ stream is converted on each pass through the cracker furnace. If, in order to accommodate the recycle of the $C_4$ stream, the fresh feedstock to the cracker has to be decreased by an amount equal to the weight of the $C_4$ stream, the overall output of the cracker will be decreased, typically by about 10% by weight, and as a result the amounts of ethene and propene produced are only about 96% and 99% by weight respectively of the amounts produced with no $C_4$ recycle.

Similar considerations apply to $C_5$ streams: while these may be used as gasoline streams or recycled to the cracker, it is often desirable to reduce the diene content thereof.

In one embodiment of the invention a $C_4$ and/or $C_5$ stream is subjected to transhydrogenation with a paraffin. Thus the polyunsaturated component of the $C_4$ and/or $C_5$ stream is used as the hydrogen-acceptor and is transhydrogenated with a paraffin containing two or more carbon atoms, particularly propane or 2-methyl propane, as the hydrogen-donor.

As a result of the reaction, the paraffin is dehydrogenated to the corresponding olefin, eg propene or 2-methylpropene, while the polyunsaturated hydrocarbons, eg butadiene, are hydrogenated to the corresponding olefins, eg n-butenes. It will be appreciated that a proportion of the olefin may be further hydrogenated to the corresponding paraffin.

We have found that this not only gives a product stream containing a substantial proportion of olefins, which may be readily recovered, but also the decreased proportion of polyunsaturated compounds gives a stream that is more readily cracked upon recycle to the cracking furnace. As a result, upon recycle of a transhydrogenated $C_4$ or $C_5$ stream to the cracking furnace, a significantly higher yield of the gaseous olefins, ethene and propene may be obtained.

The reaction may be effected with the addition of hydrogen and may typically employ 1 to 10 moles of paraffin per mole of hydrogen-acceptor hydrocarbon. Suitable catalysts include any of those mentioned above, especially chromia, optionally in admixture with a platinum group metal, on alumina, or platinum/tin on alumina.

With propane as the hydrogen-donor, the product stream will normally consist of a mixture of $C_3$ and $C_4$ hydrocarbons, predominantly propene, unreacted propane and butadiene, butenes, together with hydrogen, butanes, and some lighter hydrocarbons formed by side reactions. Where the cracker $C_4$ stream is used as such as the hydrogen-acceptor rather than a stream containing essentially only the polyunsaturated compounds separated from the cracker $C_4$ stream, the transhydrogenation product will also contain substantial amounts of 2-methylpropene and 2-methylpropane. The product stream can be separated into a light stream, a $C_3$ stream which can be fractionated into propene and propane and a $C_4$ stream. The propane recovered from the $C_3$ stream can be recycled to the transhydrogenation reactor. The transhydrogenation $C_4$ product stream may be used as a cracker feedstock. Alternatively the $C_4$ product stream may be used as a cracker feedstock. Alternatively the $C_4$ stream, preferably after purification to remove remaining butadiene, may be used as a source for the recovery of butene-1 or as a feed to a dimerisation unit to produce octenes. The use of the cracker $C_4$ stream as such as the hydrogen-acceptor gives rise to 2-methylpropene in the transhydrogenation product $C_4$ stream and this 2-methylpropene may be recovered or directly converted to MTBE. Also, the use of the cracker $C_4$ stream as such as the hydrogen-acceptor gives rise to a product $C_4$ stream containing substantial amounts of 2-methyl propane: this may render it less attractive to recover butene-1 or effect dimerisation thereof without further treatment but the use of the cracker $C_4$ stream as such as the hydrogen-acceptor has the advantage that the cost of separating the butadiene from the other $C_4$ components from the cracker $C_4$ stream is avoided.

Advantages of the transhydrogenation process over propane dehydrogenation in the absence of the hydrogen-acceptor as a method of producing propene are that much less heat need be supplied to the reactor. Indeed the reaction may be operated under thermally neutral conditions. As a result the reactor can be simpler and cheaper. Since the process can be operated with high propane conversions at lower temperatures than are required to obtain significant yields in a propane dehydrogenation reaction, less carbon deposition is liable to occur and so regeneration of the catalyst may be less frequent.

2-methylpropane can be used in place of propane as the hydrogen-donor. The reaction conditions may be similar to those employed for propane as the hydrogen-donor. The product stream will normally consist of a mixture of $C_4$ hydrocarbons, predominantly 2-methylpropene, unreacted 2-methylpropane, and n-butenes, together with hydrogen, n-butane, and some lighter hydrocarbons formed by side reactions. The 2-methylpropene may be recovered by conventional processes or the stream can be used without further purification as a feed for the production of MTBE. The unconverted $C_4$ stream from the MTBE process may be recycled to the transhydrogenation process, or to the cracking furnace as a feed for olefin production, or subjected to further processing to recover the n-butenes present.

The hydrogen can be separated from the aforementioned transhydrogenation products, obtained using propane or 2-methylpropane as the hydrogen-donor, for recycle to the transhydrogenation stage, and light, ie $C_1$ to $C_3$, hydrocarbons separated and added to an appropriate cracker stream.

Any excess of hydrogen, ie where the process is effected under net hydrogen producing conditions, can be exported, while, any shortfall of hydrogen, ie where the process is effected under net hydrogen consuming conditions, can be supplied from a suitable hydrogen stream, eg a cracker hydrogen product stream.

Unreacted paraffin, eg propane or 2-methylpropane, can be separated as a stream rich in that paraffin for recycle to the transhydrogenation reactor.

Where the remaining $C_4$ stream contains 2-methylpropene, eg as a result of using 2-methylpropane as the paraffin, the 2-methylpropene may be separated for export, eg for chemical processing. The residual $C_4$ stream consisting mainly of straight chain $C_4$ hydrocarbons which may be recycled to the cracking furnace or used for further chemical processing.

Compared to recycle of the normal cracker $C_4$ stream, recycle of the residual stream to the cracking furnace will result in a greater proportion of cracking of the recycle, because of the higher straight chain hydrocarbon content and higher degree of saturation resulting from the conversion of the polyunsaturated compounds. As a result the amount of desired gaseous olefins produced will be greater.

Where the paraffin employed is 2-methylpropane, it may be desirable not to separate a 2-methylpropane stream from the transhydrogenation product: after separation of 2-methylpropene, the 2-methylpropene-depleted $C_4$ stream may be divided into two: one part can be recycled to the transhydrogenation reactor while the remaining part is fed to the cracker furnace. In an even simpler arrangement, where a 2-methylpropene stream is not required, the transhydrogenation $C_4$ stream remaining after hydrogen and lights separation can be divided into two with one part being recycled to the transhydrogenation stage and the remainder recycled to the cracker furnace.

It will be appreciated that, for reasons of efficiency, it may be desirable to operate the process with the aforementioned separations only partial.

It is often desirable to produce an increased proportion of branched chain $C_4$ hydrocarbons, eg 2-methylpropene at the expense of straight chain $C_4$ hydrocarbons. In some cases the catalyst employed for the transhydrogenation reaction will have some isomerisation activity. Alternatively it may be desirable to employ an isomerisation catalyst before or after, or mixed with, the transhydrogenation catalyst. Isomerisation as well as transhydrogenation can thus enable a useful yield of branched chain hydrocarbons, such as 2-methylpropene, to be obtained using a straight chain hydrocarbon such as n-butane or a mixture of straight and branched chain hydrocarbons, as the hydrogen-donor.

The "others" of the cracker product include a "gasoline" stream which will include polyunsaturated compounds, eg $C_5$ polyunsaturates such as 2-methylbutadiene-1,3 pentadiene-1,3 and cyclopentadiene. Often this stream is recycled to the cracker furnace, in some cases after undergoing partial hydrogenation.

In the present invention, this "gasoline" stream, or a stream containing polyunsaturated compounds separated therefrom, may be used instead of, or in addition to, the cracker $C_4$ stream, or polyunsaturated compounds separated therefrom, as a hydrogen-acceptor stream. It will be appreciated that the transhydrogenation product will in this case contain $C_5$ compounds which can be separated for use as a low diene gasoline, or recycled to the cracker.

For use as a hydrogen-acceptor stream, the "gasoline" stream may be any one of i) a cut containing only the $C_5$ fraction; ii) a cut similar to i) but from which the cyclopentadiene has been substantially removed; iii) a full range cracker gasoline of final boiling point typically in the range 205°–210° C.; iv) depentanised iii).

The removal of any cyclopentadiene prior to transhydrogenation may be desirable since this may tend to cause excessive carbon deposition on some transhydrogenation catalysts. However if such coking can be tolerated, or catalysts employed that do not lead to excessive coke formation when cyclopentadiene is in the feed, then it will be appreciated that the $C_5$ stream can be employed as the source of the polyunsaturated hydrogen-acceptor without further treatment.

Where a "gasoline" stream is used as the hydrogen-acceptor stream, the hydrogen-donor is preferably propane, n-butene, or 2-methylpropane. If the hydrogen-donor is propane, the product from transhydrogenation is a gasoline stream of reduced diene content and a propane/propene mixture. The $C_3$ stream is readily separated from the gasoline and any light products formed in the reaction. The resultant $C_3$ stream may be fractionated to produce a propene stream and the remainder recycled to the transhydrogenation reactor. The net result is to increase the propene production from the plant together with a reduction in the hydrogen consumption required in subsequent treatment of the gasoline. Again control of the variables of the process can control the conversion to propene and the depth of hydrogenation of the gasoline stream.

Where the hydrogen-donor is 2-methylpropane or n-butane, the product will be similar except that it will contain a $C_4$ stream rather than a $C_3$ stream. If 2-methylpropane is used as the hydrogen-donor, then the resultant $C_4$ stream is useful for the manufacture of MTBE whereas if n-butane is employed, the $C_4$ stream can be used to produce a stream for the extraction of butene-1 or for the dimerisation thereof. If desired a mixed butanes stream could be used as the hydrogen-donor.

In a preferred form, the invention provides a process comprising mixing a hydrocarbon stream containing at least one polyunsaturated hydrocarbon containing 4 or 5 carbon atoms with a paraffin containing at least two carbon atoms and reacting that mixture, optionally together with hydrogen, in the presence of a dehydrogenation catalyst under condiitons effective to cause at least part of said paraffin to be dehydrogenated and at least part of the polyunsaturated hydrocarbon to be hydrogenated.

Also a preferred process for the production of olefins comprises cracking a hydrocarbon feedstock in a cracking furnace, separating from the products a stream containing predominantly $C_4$ and/or $C_5$ hydrocarbons including at least one polyunsaturated hydrocarbon, mixing a paraffin containing at least 2 carbon toms with that stream and reacting the resultant mixture, optionally together with hydrogen, in the presence of a dehydrogenation catalyst under conditions effective to cause at least part of said paraffin to be dehydrogenated and at least part of the polyunsaturated hydrocarbon to be hydrogenated, and recycling at least part of the product stream to the cracking furnace.

In a preferred form of this process, using propane or 2-methylpropane as the paraffin, at least part of the olefin produced by dehydrogenation of that paraffin, ie propene or 2-methylpropene, in the product stream is separated before any recycle to the cracking furnace. Such separation may be a physical separation process or it may involve a chemical process: for example 2-methylpropene may be selectively reacted, eg with methanol to produce MTBE, and the product of that reaction is separated. Where both 2-methylpropene and 2-methylpropane are separated from the product, it may be advantageous to remove at least part of the 2-methylpropane from the stream ahead of the 2-methylpropene removal step to reduce the total flow through the 2-methylpropene removal unit. The preferred arrangement will depend on the choice of recovery processes and local circumstances. Also, or alternatively, some or all of any unreacted paraffin may be separated eg for recycle to the transhydrogenation stage, before the remaining products are recycled to the cracker furnace.

Propadiene and/or Propyne As Hydrogen-acceptors

In the production of propene, it is usual to subject a cracker $C_3$ stream to selective hydrogenation to convert highly unsaturated components, eg propyne and propadiene, into propene, and then separate the product into a propene stream and a propane stream. In the present invention that selective hydrogenation step may be omitted and propene separated from the cracker $C_3$ stream, leaving a residual $C_3$ stream containing propane and $C_3$ polyunsaturates and this residual stream may be used as part, or all, of the hydrogen-donor stream fed to the transhydrogenation reactor. The $C_3$ polyunsaturates, ie propyne and/or propadiene, in this feed to the transhydrogenaton step act as hydrogen-acceptors in the transhydrogenation step. These hydrogen-acceptors may be augmented by polyunsaturated compounds in $C_4$ and/or $C_5$ streams as described above. Although in theory selective hydrogenation of the propyne and/or propadiene would give rise to one mole of propene for each mole of propyne or propadiene hydrogenated, in current practice this yield of propene is not realised: thus further hydrogenation takes place, typically with the formation of about one half of a mole of propene and about one half of a mole of propane for each mole of propyne or propadiene hydrogenated. By the use of propyne and/or propadiene as hydrogen-acceptors in transhydrogenation of propane as the paraffin, theoretically two moles of propene are produced for each mole of propadiene and/or propyne hydrogenated. This can result in a useful increase in the propene yield. Although the propyne and/or propadiene are preferably used to supplement poly-unsaturated compounds in a $C_4$ and/or $C_5$ hydrocarbon stream, it will be appreciated that the transhydrogenation of a paraffin, particularly propane, with propyne and/or propadiene could also be effected in the absence of any such $C_4$ and/or $C_5$ stream.

Accordingly the present invention further provides a process for olefin production comprising subjecting a hydrocarbon stream containing a) a paraffin containing at least two carbon atoms and b) propadiene and/or propyne, optionally together with hydrogen, to a dehydrogenation process in the presence of a dehydrogentation catalyst under conditions effective to cause at least part of said paraffin to be dehydrogenated and at least part of the propadiene and/or propyne to be hydrogenated.

The reaction is preferably effected with added hydrogen, steam, or methane, to minimise carbon deposition.

After separation of any light products, the product consists essentially of a mixture of propane and propene from which the propene may be recovered by conventional means. The reaction conditions may be adjusted so that the net heat output is zero by using the heat generated by the hydrogenation of the propyne and propadiene to dehydrogenate additional propane.

This reaction is particularly suited to integration with a thermal cracker producing propene. A stream containing a substantial proportion, eg up to about 40%, of propadiene and propyne can be separated by distillation from the propene stream from the cracker. Transhydrogenation of this propyne/propadiene stream enables the overall propene production to be increased.

Ethylbenzene/hydrogen-acceptor

Any suitable polyunsaturated stream, for example those described above, may be used as the hydrogen-acceptor stream to produce styrene. The choice of hydrogen-acceptor is likely to be influenced by the ease of separation of the product streams and so the use of a full range gasoline as the hydrogen-acceptor is unlikely to be attractive.

The invention is illustrated by the following examples wherein all parts and percentages are by weight unless otherwise stated. In all the examples the catalyst was reduced in a stream of hydrogen at the reaction temperature before passing the feed thereover.

EXAMPLE 1

This example demonstrates the effectiveness of transhydrogenation in promoting the production of propene. The catalyst employed was chromia on alumina (8.6% of chromium). A stream of propane (90% v/v) and nitrogen (10% v/v) was passed at 550° C. and at atmospheric pressure over the catalyst at a weight hourly space velocity of 5.9 $h^{-1}$. The composition of the effluent gas was measured at 3 min. and 23 min. after the start of the experiment. The amount of carbon formed when the experiment was terminated 23 min. after the start was also determined.

The catalyst was then regenerated by removing the carbon with an air stream followed by reduction in hydrogen at 550° C. The above procedure was then repeated using butadiene (substantially pure butadiene-1,3) in place of the nitrogen. The results are shown in Table A.

TABLE A

| | Feed composition (% by volume) | |
|---|---|---|
| propane | 90 | 90 |
| nitrogen | 10 | — |
| butadiene | — | 10 |

| | Product composition (% by weight)* | | | |
|---|---|---|---|---|
| time from start | 3 min | 23 min | 3 min | 23 min |
| hydrogen | 1.26 | 0.70 | 1.26 | — |
| methane | 0.48 | 0.37 | 1.28 | — |
| ethene | 0.12 | 0.06 | 0.27 | — |
| ethane | 0.29 | 0.08 | 1.56 | — |
| propene | 17.55 | 10.77 | 22.57 | — |
| propane | 80.29 | 88.01 | 65.89 | — |
| butadiene | — | — | 0.38 | — |
| butene-1 | — | — | 1.25 | — |
| t-butene-2 | — | — | 1.51 | — |
| c-butene-2 | — | — | 1.15 | — |
| n-butane | — | — | 2.59 | — |
| 2-methylpropene | — | — | 0.21 | — |
| 2-methylpropane | — | — | 0.08 | — |
| propene/total C3 | 0.18 | 0.11 | 0.26 | — |
| carbon g/100 g catalyst | | 0.24 | | 4.30 |
| propene kg/kg catalyst | | 0.3+ | | — |
| hydrog. heat/ dehydrog. heat (%) | 0 | 0 | 59 | — |

*excluding nitrogen.
+cumulative, ie after 23 min. a total of 0.3 kg of propene had been produced per kg of catalyst.

Table A shows that butadiene is effective in producing useful butene and butane products while reducing the amount of hydrogen produced, and thus the heat input required, while increasing the conversion of propane to propene. It is seen that the presence of butadiene enabled the propene content of the $C_3$ hydrocarbons present to be increased substantially. It is seen from Table A that where butadiene was present in the feed, the heat of hydrogenation of the butadiene (assumed to be hydrogenated to butene-1 for the purposes of calculation) is 59% of the heat required for dehydrogenating the propane. If the further heat released by the further hydrogenation of butenes to butanes is also added, together with the additional heat resulting from the formation of 2-methylpropene, t-butene-2, and c-butene-2, rather than assuming all the butadiene was hydrogenated to butene-1, the heat of hydrogenation amounts to about 88% of the heat required for the dehydrogenation of the propane.

The above procedure was repeated at different temperatures, in each case using a fresh sample of catalyst, and the composition of the effluent gas was measured after 3 min. on-line. In the case of the dehydrogenation in the presence of butadiene, the the butadiene was converted to a mixture of n-butenes and n-butane. In Table B there are shown the propene/total $C_3$ ratio (as a weight percentage) of the product together with the ratio that would be obtained if equilibrium had been achieved. In the case of the feed containing butadiene, the ratio of the heat of hydrogenation of the butadiene to the heat of dehydrogenation of the propane is quoted, calculated from the found conversions.

TABLE B

|  | Temperature (°C.) | | | |
| --- | --- | --- | --- | --- |
|  | 400 | 450 | 500 | 550 |
| 10% v/v nitrogen in feed | | | | |
| product propene/total C3 at equilibrium (% wt) | 4.0 | 8.9 | 17.7 | 31.3 |
| found (% wt) | — | 1.8 | 7.4 | 18.7 |
| 10% v/v butadiene in feed | | | | |
| product propene/total C3 at equilibrium (% wt) | 17.7 | 20.2 | 26.5 | 37.9 |
| found (% wt) | 2.5 | 8.4 | 16.2 | 25.6 |
| hydrog/dehydrog heat (%) | >100 | >100 | 99 | 58 |

EXAMPLE 2

A stream of propane (80% v/v) and substantially pure butadiene-1,3 (20% v/v) was passed at 550° C. and at atmospheric pressure over a fresh sample of the catalyst used in Example 1 at a weight hourly space velocity of 5.4 $h^{-1}$. The composition of the effluent gas was measured at 3 min. and 23 min. after the start of the experiment. The amount of carbon formed was also determined.

The catalyst was then regenerated by removing the carbon with an air stream followed by reduction in hydrogen at 550° C. The above procedure was then repeated using the above propane/butadiene stream that had been diluted with an equal volume of hydrogen. The composition of the effluent gas was determined after 3, 23, and 123 min. from the start of the experiment, and the reaction was continued for a total of 145 min. The results are shown in Table C.

TABLE C

|  | Feed composition (% by volume) | |
| --- | --- | --- |
| propane | 80 | 40 |
| butadiene | 20 | 10 |
| hydrogen |  | 50 |

|  | Product composition (% by weight) | | | | |
| --- | --- | --- | --- | --- | --- |
| time from start | 3 min | 23 min | 3 min | 23 min | 123 min |
| hydrogen | 0.76 | 0.28 | 3.50 | 3.37 | 3.27 |
| methane | 0.46 | 0.41 | 1.26 | 1.13 | 0.56 |
| ethene | 0.19 | 0.23 | 0.23 | 0.23 | 0.17 |
| ethane | 0.36 | 0.19 | 2.03 | 1.57 | 0.58 |
| propene | 12.40 | 5.46 | 15.36 | 14.85 | 10.50 |
| propane | 72.57 | 77.65 | 61.10 | 62.42 | 67.56 |
| butadiene | 1.23 | 4.90 | 0.52 | 0.56 | 0.80 |
| butene-1 | 3.30 | 3.46 | 2.49 | 2.66 | 3.84 |
| t-butene-2 | 3.89 | 4.01 | 2.82 | 3.02 | 4.36 |
| c-butene-2 | 2.99 | 3.10 | 2.18 | 2.33 | 3.38 |
| n-butane | 1.46 | 0.24 | 7.62 | 7.06 | 4.62 |
| 2-methylpropene | 0.35 | 0.05 | 0.58 | 0.55 | 0.29 |

TABLE C-continued

| 2-methylpropane | 0.05 | 0.03 | 0.31 | 0.24 | 0.07 |
| --- | --- | --- | --- | --- | --- |
| propene/total C3 | 0.15 | 0.07 | 0.20 | 0.19 | 0.14 |
| carbon g/100 g catalyst |  | 7.70 |  |  | 5.60[+] |
| propene kg/kg catalyst |  | 0.2 |  |  | 0.8[+] |
| hydrog. heat/ dehydrog. heat (%) | >100 | — | >100 | >100 | >100 |

[+]after 145 min

Comparison with Table A shows that at the higher butadiene content employed in the initial part of Example 2, the catalyst activity died off rapidly; thus after 23 min. the results show that there was no net dehydrogenation of propane. However the second part of the example shows that the presence of substantial amounts of hydrogen reduced the rate of carbon formation.

EXAMPLE 3

To illustrate the advantage of the presence of a hydrogen-acceptor in a dehydrogenation process, calculations were performed of the equilibrium concentration of propene in the catalytic dehydrogenation of propane at 500° C. and 550° C. at atmospheric pressure in the absence of a hydrogen-acceptor and in the presence of an equimolar amount of pure butadiene-1,3 as a hydrogen-acceptor.

At equilibrium at a temperature of 500° C., propene forms 17% by weight of the $C_3$ hydrocarbons present when no butadiene is present and 3163 kJ of heat are required per kg of propene produced. At equilibrium at 550° C., the corresponding figures are 32% by weight and 3079 kJ per kg of propene produced.

However when an equimolor amount of butadiene is present, at 500° C. the equilibrium propene content is 74% by weight of the total $C_3$ hydrocarbons present and the heat input required is only 69 kJ per kg of propene produced. At 550° C., the corresponding figures are 76% by weight and 138 kJ per kg of propene produced.

EXAMPLE 4

To illustrate that a thermally neutral process could be achieved for the dehydrogenation of propane in the presence of a hydrogen-acceptor, calculations were performed of the equilibrium concentration of propene when effecting catalytic dehydrogenation thereof at a total pressure of 20 bar abs. in the presence of steam and 1 mole of an equimolar mixture of propyne and propadiene for each 4 moles of propane, there being 8 moles of steam to each mole of hydrocarbon. Calculation showed that at a temperature of 557° C. at equilibrium propene represented 46% by weight of the total $C_3$ components and at that temperature the reaction would be thermally neutral, ie the heat of reaction was 0 kJ per kg of propene produced.

EXAMPLE 5

Propane was catalytically dehydrogenated in the presence of hydrogen and a $C_4$ stream typical of the product from steam cracking a hydrocarbon feedstock. The catalyst employed was platinum/tin on alumina (1% of a Pt/Sn mixture having a Pt/Sn weight ratio of 1:1). A mixture of propane (about 40% v/v), hydrogen (about 50% v/v), and $C_4$ stream (about 10% v/v), was passed at atmospheric pressure over the catalyst at 550° C. at a weight hourly space velocity of 3.5 h$^{-1}$. The composition of the feed gas and the effluent gas at various times on-line is shown in Table D. In each case the calculated heat of hydrogenation of the butadine exceeds the calculated heat of dehydrogenation of the propane.

TABLE D

|  | Composition (wt %) after N hours on-line | | | |
| --- | --- | --- | --- | --- |
|  | Feed | N = 0.15 | N = 0.8 | N = 2.73 |
| hydrogen | 3.8 | 3.7 | 3.6 | 3.6 |
| lights | 0.0 | 0.8 | 0.6 | 0.5 |
| propane | 76.2 | 66.8 | 66.9 | 67.0 |
| propene | 0.0 | 9.2 | 9.1 | 8.9 |
| 2-methylpropane | 0.4 | 4.1 | 4.1 | 3.9 |
| 2-methylpropene | 4.7 | 2.5 | 2.5 | 2.5 |
| n-butane | 1.4 | 8.8 | 9.1 | 9.4 |
| n-butenes | 4.3 | 3.9 | 3.9 | 4.0 |
| butadiene | 9.2 | 0.1 | 0.1 | 0.1 |
| coke | — | 0.07 | 0.07 | 0.07 |

It is seen from this example that this catalyst also exhibits some isomerisation activity: thus some isomerisation took place with the formation of branched chain C$_4$ hydrocarbons, viz 2-methylpropane and 2-methylpropene, at the expense of the straight chain C$_4$ hydrocarbons, n-butane, n-butenes and butadiene.

EXAMPLE 6

Propane was catalytically dehydrogenated at 620° C. at a pressure of 3 bar abs. in the presence of a C$_4$ stream typical of the product from steam cracking a hydrocarbon feedstock, and in the presence of hydrogen. The weight hourly space velocity of the gas mixture was 10.1 h$^{-1}$. The catalyst employed was chromia (7.6% chromium) on an alumina support that had been neutralised by the addition of potassium. The feed composition and product composition after 10 min. on line are shown in Table E. The rate of propene formation corresponded to about 1.2 kg of propene per kg of catalyst per hour. The calculated heat of hydrogenation of the butadiene exceeded the heat required for dehydrogenation of the propane.

TABLE E

|  | composition (% wt) | |
| --- | --- | --- |
|  | feed | 10 min on-line |
| hydrogen | 3.8 | 3.8 |
| lights | 0.0 | 1.7 |
| propene | 0.0 | 12.1 |
| propane | 76.2 | 62.8 |
| 2-methylpropane | 0.4 | 2.3 |
| 2-methylpropene | 4.7 | 2.7 |
| n-butane | 1.4 | 7.5 |
| n-butenes | 4.3 | 6.7 |
| butadiene | 9.2 | 0.2 |
| coke | — | 0.2 |

EXAMPLE 7

Propane was catalytically dehydrogenated at atmospheric pressure and at 550° C. in the presence of hydrogen and, as a hydrogen acceptor stream, a C$_4$ stream typical of a cracker C$_4$ stream. The weight hourly space velocity of the gas mixture was 4.7 h$^{-1}$. The catalyst was a sulphur moderated platinum on alumina (0.7% Pt). The feed composition and the product composition after 27 min. on-line is shown in Table F. The calculated heat of hydrogenation of the butadiene exceeded the heat required for dehydrogenation of the propane.

TABLE F

|  | composition (% wt) | |
| --- | --- | --- |
|  | feed | 27 min on-line |
| hydrogen | 3.8 | 3.7 |
| lights | 0.0 | 2.7 |
| propene | 0.0 | 8.9 |
| propane | 76.2 | 67.9 |
| 2-methylpropane | 0.4 | 3.3 |
| 2-methylpropene | 4.7 | 2.0 |
| n-butane | 1.4 | 7.6 |
| n-butenes | 4.2 | 3.3 |
| butadiene | 9.3 | 0.1 |
| coke | — | 0.5 |

EXAMPLE 8

Propane was catalytically dehydrogenated at atmospheric pressure and at 575° C. in the presence of hydrogen and, as a hydrogen acceptor stream, a mixture of a C$_4$ stream typical of a cracker C$_4$ stream, propyne, and propadiene. The weight hourly space velocity of the gas mixture was 3.3 h$^{-1}$. The catalyst was a fresh sample of that used in Example 6. The feed composition and the product composition after 3 min. on-line is shown in Table G. The calculated heat of hydrogenation of the butadiene, propyne, and propadiene was 75% of the heat required for dehydrogenation of the propane.

TABLE G

|  | composition (% wt) | |
| --- | --- | --- |
|  | feed | 3 min on-line |
| hydrogen | 3.5 | 3.6 |
| lights | 0.0 | 2.6 |
| propene | 0.0 | 15.7 |
| propane | 76.3 | 59.6 |
| propyne/propadiene | 1.9 | 0.0 |
| 2-methylpropane | 0.4 | 2.2 |
| 2-methylpropene | 4.3 | 2.4 |
| n-butane | 1.3 | 6.8 |
| n-butenes | 3.9 | 6.4 |
| butadiene | 8.4 | 0.3 |
| coke | — | 0.4 |

EXAMPLE 9

2-methyl propane was catalytically dehydrogenated at atmospheric pressure in the presence of a C$_4$ stream typical of the product from steam cracking a hydrocarbon feedstock, and in either the presence or the absence of hydrogen. The catalyst employed was chromia (7.6% chromium) on an alumina support that had been neutralised by the addition of potassium. The feed compositions, temperatures, and weight hourly space velocities are shown in Table H.

TABLE H

| Time on-line (min.) | feed | 3 | 3 | feed | 33 |
| --- | --- | --- | --- | --- | --- |
| Temperature (°C.) |  | 550 | 500 |  | 550 |
| Space velocity (h$^{-1}$) |  | 7.2 | 7.2 |  | 3.2 |
| composition (% wt) |  |  |  |  |  |
| hydrogen | 0.0 | 1.2 | 0.6 | 4.5 | 4.6 |
| lights | 0.0 | 2.8 | 1.1 | 0.0 | 1.4 |
| 2-methylpropane | 81.2 | 43.2 | 58.4 | 76.8 | 57.1 |
| 2-methylpropene | 4.4 | 38.9 | 26.1 | 4.4 | 23.0 |

TABLE H-continued

| | | | | | |
|---|---|---|---|---|---|
| n-butane | 1.5 | 5.3 | 5.6 | 1.4 | 9.0 |
| n-butenes | 4.0 | 6.6 | 7.1 | 4.0 | 4.8 |
| butadiene | 8.9 | 0.4 | 0.2 | 8.9 | 0.1 |
| coke | — | 1.6 | 0.9 | — | 0.02 |
| hydrog. heat/ dehydrog. heat (%) | — | 32 | 53 | — | 63 |

EXAMPLE 10

2-methylpropane was catalytically dehydrogenated at atmospheric pressure and at 550° C. in the presence of hydrogen and, as a hydrogen acceptor stream, a $C_5$ gasoline stream from which cyclopentadiene had been removed. The weight hourly space velocity of the gas mixture was 3 $h^{-1}$. The catalyst was fresh sample of that used in Example 6. The feed composition and the product composition after 5 min. on-line is shown in Table I.

The calculated heat of hydrogenation of the pentadienes was about 32% of the heat required for dehydrogenation of the 2-methylpropane.

TABLE I

| | composition (% wt) | |
|---|---|---|
| | feed | 5 min on-line |
| hydrogen | 3.7 | 4.0 |
| lights | 0.0 | 1.4 |
| n-C4 hydrocarbons | 0.1 | 0.9 |
| 2-methylpropane | 81.2 | 58.8 |
| 2-methylpropene | 0.0 | 20.1 |
| pentanes | 5.4 | 7.5 |
| pentenes | 3.0 | 6.2 |
| pentadienes | 6.6 | 0.8 |
| coke | — | 0.3 |

EXAMPLE 11

A mixture of a $C_4$ stream from a cracker having the composition set out in Table J, 2-methylpropane, and hydrogen in the approximate proportions of $C_4$ stream 19%, 2-methylpropane 77%, and hydrogen 4% (which corresponds to approximately 1.3 moles of hydrogen per mole of total hydrocarbon) was subjected to transhydrogenation using a chromia/alumina catalyst at 550° C. at atmospheric pressure at a weight hourly space velocity of 4 $h^{-1}$. The feed and product compositions were as shown in Table J.

TABLE J

| | Composition (% w/w) | | |
|---|---|---|---|
| | Cracker C4 stream | Transhydrogenation | |
| | | feed | product |
| hydrogen | | 4.4 | 4.6 |
| methane | | | 0.7 |
| ethane | | | 0.3 |
| ethene | | | 0.0 |
| propane | | | 1.1 |
| propene | | | 0.7 |
| butadiene | 50.8 | 9.6 | 0.2 |
| butene-1 | 11.8 | 2.2 | 1.8 |
| t-butene-2 | 4.3 | 0.8 | 2.1 |
| c-butene-2 | 3.3 | 0.6 | 1.7 |
| 2-methylpropene | 21.4 | 4.0 | 21.3 |
| n-butane | 6.7 | 1.3 | 7.1 |
| 2-methylpropane | 1.7 | 77.1 | 58.3 |

Calculation shows that the heat of hydrogenation of the butadiene amounted to 71% of the heat required for dehydrogenation of the 2-methylpropane. If the heat of further hydrogenation to n-butane, and the additional heat produced as a result of the formation of t-butene-2 and c-butene-2, rather than butene-1, is included, the heat of hydrogenation of the butadiene exceeds the heat required for dehydrogenation of the 2-methylpropane.

If the product is subjected to separation stages to separate hydrogen (for recycle to the transhydrogenation stage), light ($C_1$ to $C_3$) hydrocarbons (for addition to the cracker product), 2- methylpropene, and 2-methylpropane (for recycle to the transhydrogenation stage), the residual $C_4$ stream contains only straight chain hydrocarbons. The amount of 2-methylpropene recoverable is about 5 times the amount of 2-methylpropene in the cracker $C_4$ stream. From the hydrogen content of the transhydrogenation product, it is seen that the reaction is effected under slight hydrogen generating conditions. The amount of the residual stream, (ie the $C_4$ stream remaining after separation of the hydrogen, light hydrocarbons, and branched $C_4$ hydrocarbons), is about 68.6% of the original $C_4$ cracker stream.

From knowledge of the cracking patterns of the individual components, calculation shows that if 686 parts of this residual stream were to be recycled to a typical cracker furnace, about 90% of the residual stream would be cracked with the production of the amounts of product shown in Table K. Table K also shows the amounts of product that would be obtained if 1000 parts of the original $C_4$ cracker stream was recycled directly to the cracker furnace.

It is seen from Table K that this procedure enables more valuable light olefinic products to be produced from the cracker than if the original cracker $C_4$ stream is simple recycled.

TABLE K

| | Amounts (parts) of products from cracking | |
|---|---|---|
| | Residual C4 stream from transhydrogenation | Original cracker C4 stream |
| hydrogen | 5 | 6 |
| methane | 132 | 130 |
| ethene | 196 | 170 |
| propene | 161 | 145 |
| C4 hydrocarbons | 69 | 200 |
| benzene | 51 | 120 |
| toluene | 16 | 50 |
| C8 aromatics | 12 | 30 |
| fuel oil | 30 | 50 |
| others | 14 | 99 |
| total | 686 | 1000 |

EXAMPLE 12

A mixture of a $C_4$ stream from a cracker having the composition set out in Table L below, propane, and hydrogen in the approximate proportions of $C_4$ stream 20%, propane 76%, and hydrogen 4% (which corresponds to approximately 1 mole of hydrogen per mole of total hydrocarbon, and about 4.8 moles of propane per mole of $C_4$ hydrocarbon) was subjected to transhydrogenation using a chromia/alumina catalyst at 570° C. at atmospheric pressure at a weight hourly space velocity of 3.3 $h^{-1}$. The measured transhydrogenation feed and product compositions were as shown in Table L.

Calculation shows that the heat of hydrogenation of the butadiene amounted to 75% of the heat required for dehydrogenation of the propane. If the heat of further hydrogenation to n-butane, and the additional heat produced by as a result of the formation of t-butene-2 and c-butene-2, rather than butene-1, is included, the heat of hydrogenation of the butadiene exceeds the heat required for dehydrogenation of the propane.

TABLE L

| | Composition (% w/w) | | |
|---|---|---|---|
| | Cracker C4 stream | Transhydrogenation feed | product |
| hydrogen | | 3.9 | 3.9 |
| methane | | | 0.7 |
| ethane | | | 0.9 |
| ethene | | | 0.1 |
| propane | | 75.8 | 60.9 |
| propene | | | 14.8 |
| butadiene | 50.8 | 10.3 | 0.4 |
| butene-1 | 11.8 | 2.4 | 2.2 |
| t-butene-2 | 4.3 | 0.9 | 2.5 |
| c-butene-2 | 3.3 | 0.7 | 2.0 |
| 2-methylpropene | 21.4 | 4.3 | 2.5 |
| n-butane | 6.7 | 1.4 | 7.0 |
| 2-methylpropane | 1.7 | 0.3 | 2.2 |

The transhydrogenation product may be subjected to the following series of separation stages:

a) hydrogen separation (for recycle to the transhydrogenation stage and/or export), b) light ($C_1$ to $C_2$) hydrocarbons separation (for addition to the cracker product), c) separation of a $C_3$ stream: the separated $C_3$ stream may be further separated into a propene product stream, eg in the $C_3$ splitter stage of an associated olefins plant. From the $C_3$ splitter, the propane stream may be recycled to the transhydrogenation stage, and, optionally, d) butenes separation.

The residual $C_4$ stream remaining after butenes separation and consisting essentially of about 11 parts of 2-methylpropane and 35 parts of n-butane for each 100 parts of the $C_4$ stream fed to the transhydrogenation stage, can be recycled to the cracker.

Alternatively, the $C_4$ stream remaining after separation of the $C_3$ stream can be recycled without separation of butenes. For each 1000 parts of the original $C_4$ stream fed to the transhydrogenation stage, this residual, butenes containing, $C_4$ stream amounts to about 930 parts. From knowledge of the cracking patterns of the individual components, calculation shows that if these 930 parts of the butenes-containing $C_4$ stream were to be recycled to a typical cracker furnace, about 90% of the components would be cracked with the production of the amounts of product shown in Table M. Table M also shows the amounts of product that would be obtained if the 1000 parts of the original $C_4$ cracker stream was recycled directly to the cracker furnace.

TABLE M

| | Amounts (parts) of products from cracking | |
|---|---|---|
| | Residual C4 stream from transhydrogenation | Original cracker C4 stream |
| hydrogen | 6 | 6 |
| methane | 177 | 130 |
| ethene | 239 | 170 |
| propene | 231 | 145 |
| C4 hydrocarbons | 93 | 200 |
| benzene | 79 | 120 |

TABLE M-continued

| | Amounts (parts) of products from cracking | |
|---|---|---|
| | Residual C4 stream from transhydrogenation | Original cracker C4 stream |
| toluene | 25 | 50 |
| C8 aromatics | 18 | 30 |
| fuel oil | 48 | 50 |
| others | 14 | 99 |
| total | 930 | 1000 |

As in Example 11, it is seen that this enables more valuable light olefinic products to be produced from the cracker than if the original cracker $C_4$ stream is simply recycled.

We claim:

1. A process for the production of olefins comprising dehydrogenating at least one hydrogen-donor hydrocarbon that is free from olefinic unsaturation in the presence of a dehydrogenation catalyst and in the presence of at least one hydrogen-acceptor hydrocarbon that is more highly unsaturated than a mono-olefin under conditions effective to cause at least part of said hydrogen-donor hydrocarbon to be dehydrogenated and at least part of the hydrogen-acceptor to be hydrogenated, characterised in that the amount of said hydrogen-acceptor is such that there are 0.5 to 20 moles of said hydrogen-donor for each mole of hydrogen-acceptor, and the amount of said hydrogen-acceptor hydrocarbon hydrogenated is such that the heat of hydrogenation of said hydrogen-acceptor hydrocarbon provides at least 25% of the heat required for dehydrogenation of said hydrogen-donor hydrocarbon.

2. A process according to claim 1 wherein there are 1 to 10 moles of said hydrogen-donor for each mole of hydrogen-acceptor.

3. A process according to claim 1 or claim 2 wherein said hydrogen-donor hydrocarbon comprises at least one paraffin selected from propane, 2-methylpropane, and n-butane.

4. A process according to claim 1 which comprises using a stream comprising hydrocarbons having from 4 to 5 carbon atoms, including said at least one hydrogen-acceptor hydrocarbon, and a stream containing at least one paraffin containing at least two carbon atoms as said hydrogen-donor.

5. A process according to claim 1 which comprises using a stream comprising hydrocarbons having from 4 to 5 carbon atoms and at least one hydrogen-acceptor comprising propyne and propadiene separated from the products of cracking a hydrocarbon feedstock in a cracking furnace.

6. A process according to claim 5 which comprises recycling at least part of the product reduced in propyne and propadiene content to the cracking furnace.

7. A process according to claim 1 wherein said at least one hydrogen-donor comprises a member of the group consisting of propane and 2-methylpropane, and said hydrogen-acceptor comprises a member of the group consisting of propadiene and propyne separated from the products of cracking a hydrocarbon feedstock in a cracking furnace.

8. A process according to claim 1 wherein said at least one hydrogen-acceptor hydrocarbon comprises a member of the group consisting of propadiene and propyne, and said at least one hydrogen-donor hydrocarbon comprises a paraffin containing at least two carbon atoms.

9. A process according to claim 1 which comprises dehydrogenating in the presence of a member of the group consisting of hydrogen, steam, and methane.

* * * * *